(12) United States Patent
Chen et al.

(10) Patent No.: US 8,973,565 B2
(45) Date of Patent: Mar. 10, 2015

(54) DEVICE AND METHOD FOR INDUCING BRAIN INJURY IN ANIMAL TEST SUBJECTS

(75) Inventors: Zhiyong Chen, Gaithersburg, MD (US);
Zhilin Liao, Rockville, MD (US);
Frank C. Tortella, Columbia, MD (US);
Xi-Chun May Lu, Laurel, MD (US);
Jitendra R. Dave, Gaithersburg, MD (US); Jay E. Bartlett, Adamstown, MD (US); Mark F. Arnold, Shepherdstown, WV (US); Mark P. Easterday, Jefferson, MD (US); Mark W. Brown, Meyersville, MD (US); Larry R. Holmes, Peach Bottom, PA (US); Zachary J. Larimore, Elkton, MD (US); Kara E. Schmid, Germantown, MD (US); Deborah A. Shear, Ellicott City, MD (US); Lai Yee Leung, Bethesda, MD (US); Andrea Mountney, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 26 days.

(21) Appl. No.: 13/507,945

(22) Filed: Aug. 8, 2012

(65) Prior Publication Data
US 2013/0042332 A1 Feb. 14, 2013

Related U.S. Application Data

(60) Provisional application No. 61/521,446, filed on Aug. 9, 2011.

(51) Int. Cl.
*F41B 11/32* (2006.01)

(52) U.S. Cl.
USPC ............................... 124/56; 800/9; 119/850

(58) Field of Classification Search
USPC ................................... 124/56; 800/9; 119/850
See application file for complete search history.

(56) References Cited

U.S. PATENT DOCUMENTS

| | | | | |
|---|---|---|---|---|
| 3,782,018 A | * | 1/1974 | Hancox | 42/1.12 |
| 3,996,644 A | * | 12/1976 | Andersson | 452/58 |
| 4,353,147 A | * | 10/1982 | Nijhuis | 452/53 |
| 4,571,777 A | * | 2/1986 | Nijhuis | 452/54 |
| 4,575,900 A | * | 3/1986 | Hamel et al. | 452/62 |
| 4,748,719 A | * | 6/1988 | Bowman et al. | 452/54 |
| 5,326,307 A | * | 7/1994 | Bernardus et al. | 452/58 |
| 5,486,145 A | * | 1/1996 | Dorsthorst et al. | 452/58 |
| 5,692,951 A | * | 12/1997 | Huff | 452/62 |
| 5,727,996 A | * | 3/1998 | Newton | 452/57 |
| 6,001,011 A | * | 12/1999 | Johnson | 452/65 |
| 6,183,356 B1 | * | 2/2001 | Middleton et al. | 452/57 |

(Continued)

*Primary Examiner* — Michael David
(74) *Attorney, Agent, or Firm* — Caroline Nash; Elizabeth Arwine

(57) ABSTRACT

An apparatus and method for inflicting brain injury on a laboratory animal that employs a platform for supporting the laboratory animal. The platform defines an opening for positioning the head of the laboratory animal over the opening. A projectile is launched from a projectile launching device orientated below the opening of the platform. The projectile launching device has a means for propelling the projectile directly at and/or through the opening of said platform, thereby inflicting brain injury on the animal via either a pressure wave or concussive impact of the projectile. Without helmet, direct impact of the projectile results in severe traumatic brain injury. Use of helmet protects animals from skull fracture, subdural hematoma, intracerebral hemorrhage and contusion yet produces mild concussion-like pathology.

50 Claims, 22 Drawing Sheets

(56) References Cited

U.S. PATENT DOCUMENTS

| | | | |
|---|---|---|---|
| 6,769,976 B2 * | 8/2004 | Bass | 452/62 |
| 7,220,177 B2 * | 5/2007 | King et al. | 452/62 |
| 7,575,507 B2 * | 8/2009 | King et al. | 452/57 |
| 7,927,194 B2 * | 4/2011 | Jurs et al. | 452/135 |
| 7,980,925 B2 * | 7/2011 | Bass | 452/57 |
| 2003/0171085 A1 * | 9/2003 | Bass | 452/62 |
| 2007/0011935 A1 * | 1/2007 | Bass | 43/17.1 |

* cited by examiner

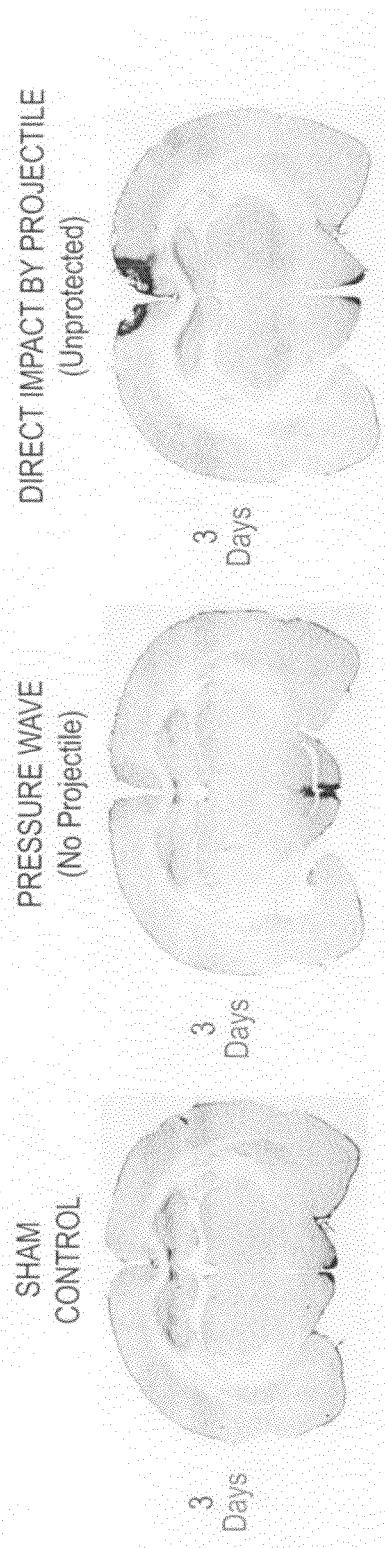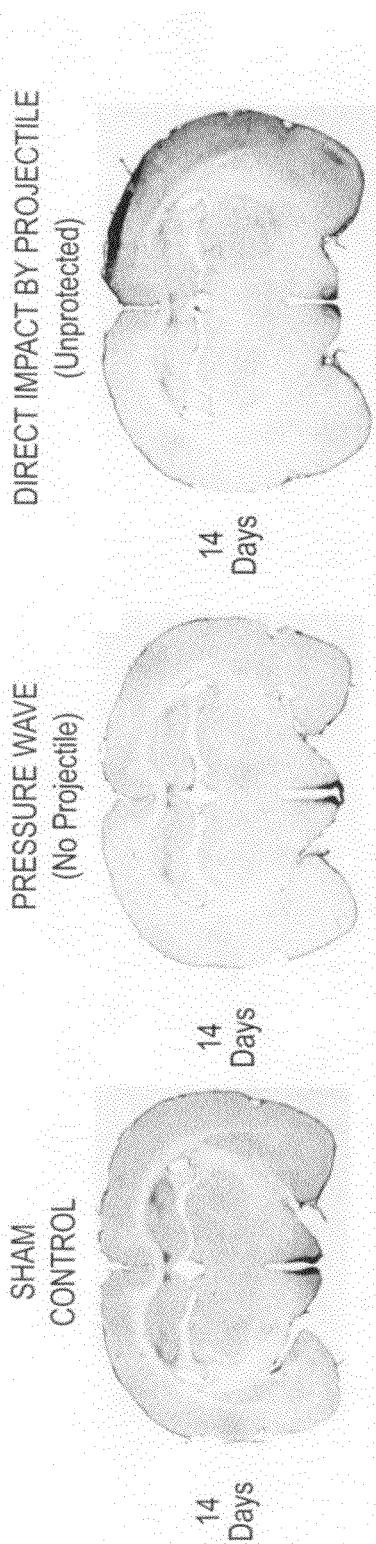

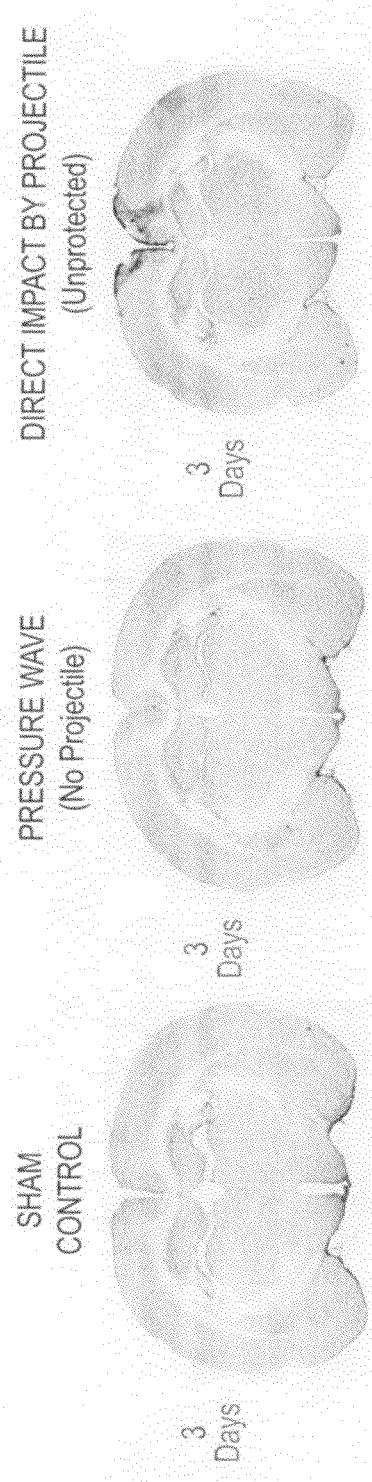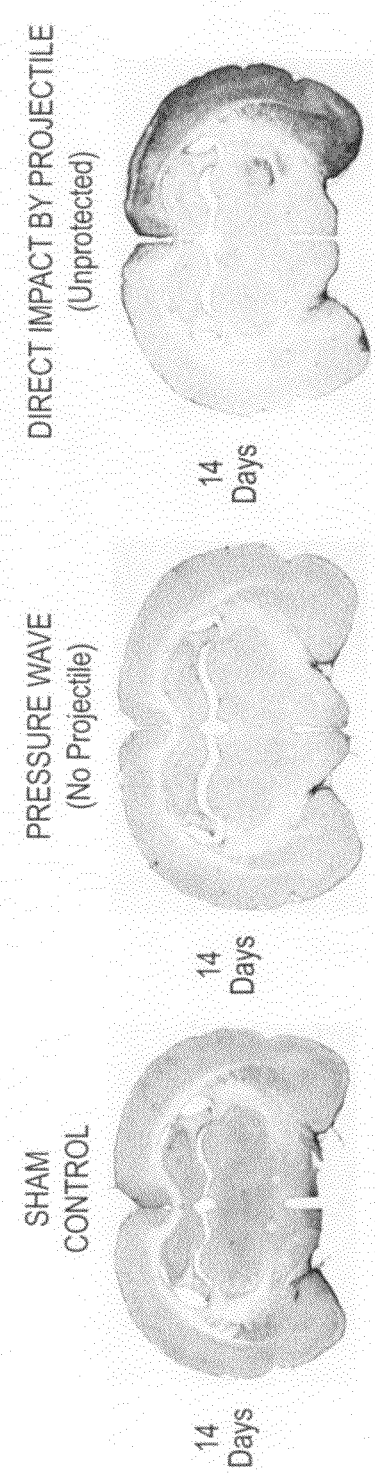

SHAM CONTROL
3 Days

PRESSURE WAVE (No Projectile)
3 Days

DIRECT IMPACT BY PROJECTILE (Unprotected)
3 Days

SHAM CONTROL
14 Days

PRESSURE WAVE (No Projectile)
14 Days

DIRECT IMPACT BY PROJECTILE (Unprotected)
14 Days

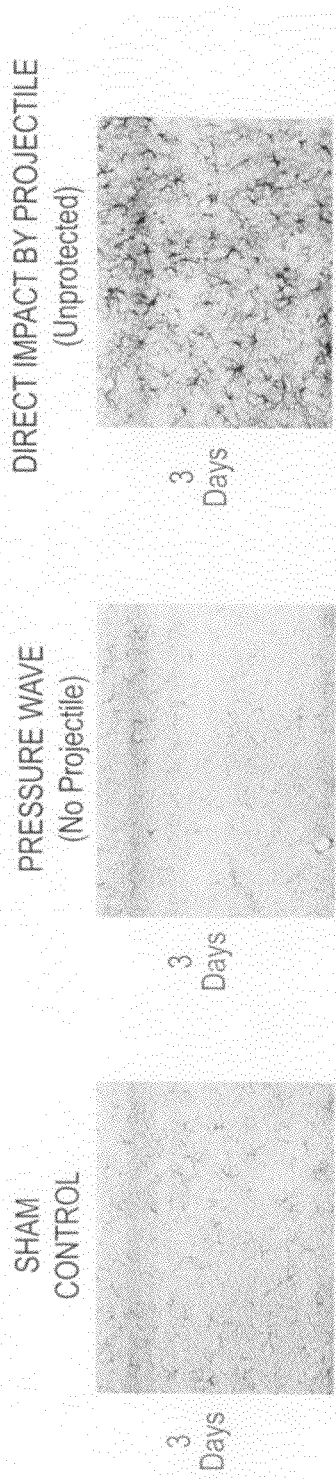
FIG. 12a SHAM CONTROL 3 Days
FIG. 12b SHAM CONTROL 14 Days
FIG. 12c PRESSURE WAVE (No Projectile) 3 Days
FIG. 12d PRESSURE WAVE (No Projectile) 14 Days
FIG. 12e DIRECT IMPACT BY PROJECTILE (Unprotected) 3 Days
FIG. 12f DIRECT IMPACT BY PROJECTILE (Unprotected) 14 Days

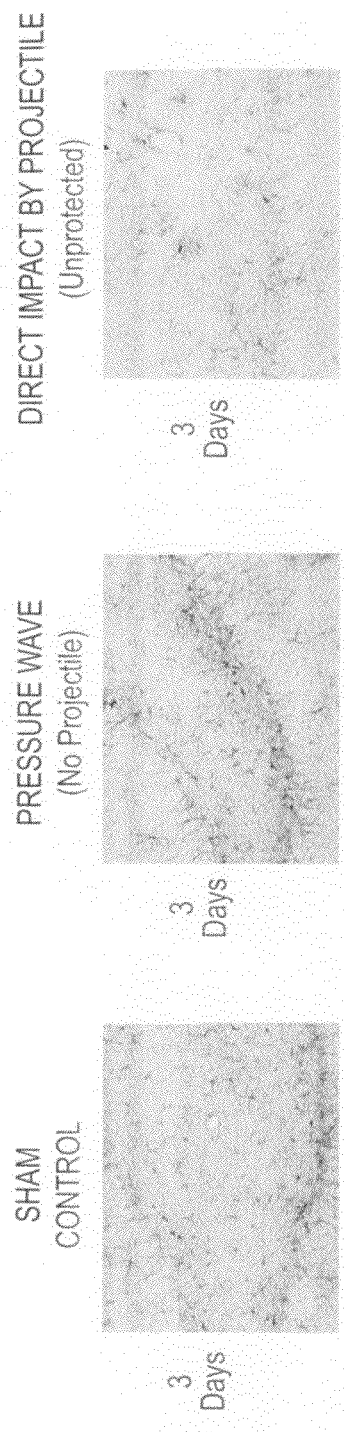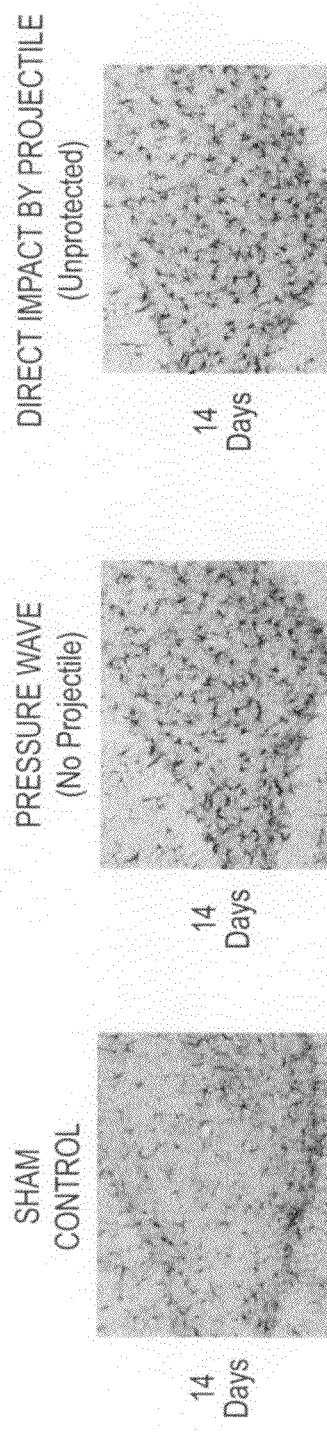
FIG. 13a SHAM CONTROL 3 Days
FIG. 13c PRESSURE WAVE (No Projectile) 3 Days
FIG. 13e DIRECT IMPACT BY PROJECTILE (Unprotected) 3 Days
FIG. 13b SHAM CONTROL 14 Days
FIG. 13d PRESSURE WAVE (No Projectile) 14 Days
FIG. 13f DIRECT IMPACT BY PROJECTILE (Unprotected) 14 Days

DEVICE AND METHOD FOR INDUCING BRAIN INJURY IN ANIMAL TEST SUBJECTS

This invention claims priority of U.S. Provisional Application Ser. No. 61/521,446 filed on Aug. 9, 2011.

GOVERNMENT INTEREST

This invention was made with support from the United States Government, specifically the Walter Reed Army Institute of Research, and; accordingly, the United States Government has certain rights in this invention.

BACKGROUND OF THE INVENTION

1. Field of the Invention

The present invention relates a device and method for inducing traumatic brain injury (TBI) in animal test subjects. Specifically, the invention is (1) a device driven by compressed gases and method for launching a small projectile designed to impact a target and (2) a protective custom-designed small animal helmet that uses pressure sensor film to measure the force/distribution of the impact pressure on both the outer and inner surfaces of the helmet.

2. Brief Description of Related Art

Traumatic brain injury (TBI) has been identified as a significant public health concern affecting over 1.7 million people each year in the United States alone. The vast majority of nonfatal TBIs (75%) in military have been classified as "mild" (mTBI) typically caused by closed-head concussion (Gerberding J L and Binder S. 2003. Report to Congress on Mild Traumatic Brain Injury in the United States: Steps to Prevent a Serious Public Health Problem. In: *National Center for Injury Prevention and Control, Centers for Disease Control and Prevention*). Because of the high use of improvised explosive devices (IEDs) in war, there has been increased concern regarding combat-related concussions sustained by U.S. military personnel (Owens B D, Kragh J F, Jr., Wenke J C, Macaitis J, Wade C E and Holcomb J B. (2008). Combat wounds in operation Iraqi Freedom and operation Enduring Freedom. J Trauma. 64:295-299). It has been estimated that up to 28% of U.S. military personnel sustained at least one concussive mTBI event while deployed in Iraq and Afghanistan (Warden D. (2006). Military TBI during the Iraq and Afghanistan wars. J Head Trauma Rehabil. 21:398-402). Moreover, the emergence of the mTBI casualty during OIF and OEF and the extremely high incidence of which it has occurred in our soldiers has defined this combat wound as the "signature injury" of these wars. From the period 2000 through 2010, over 200,000 cases of TBI were diagnosed in the military (http://www.health.mil/Research/TBI_Numbers.aspx), with over 75% of these injuries classified as mTBI. Importantly, combat troops are often exposed to more than one concussion or mTBI in a short timeframe, the cumulative effects of which can produce long-lasting effects including physical, mental, emotional and cognitive impairments and may place our returning soldiers at increased risk for PTSD and/or neurodegenerative disorders.

Despite the high incidence of closed-head concussive mTBI in civilian and military sectors, objective diagnostic tools and knowledge about what occurs in the brain following this type of injury are limited. Ideally, the diagnosis or treatment of mTBI would be based upon understanding the injurious changes in the brain on a cellular level. However, concussive-impact induced mTBI does not produce structural changes detectable by conventional neuroimaging techniques, making clinical diagnosis challenging, particularly in the presence of more obvious injuries. Much of what has been learned about concussion in the past decade has been acquired through the systematic study of concussion sustained in sports. Currently, the clinical diagnosis of mTBI relies on symptom reporting and neurological exams, such as the Sport Concussion Assessment Tool 2 (SCAT2) National Football League (NFL) sideline exam and the Military Acute Concussion Evaluation (MACE). However, these tests typically require baseline scores for clear interpretation and rely heavily on self-reported symptoms and subjective evaluations. Increased understanding of the complex pathophysiological processes affecting the brain as a result of concussion may provide more objective diagnostic tools and improve guidelines for managing cerebral concussion for both our military population and the civilian population.

In order to study experimentally-induced concussion in animal test subjects that is clinically relevant, we have developed a device and method for producing closed-head projectile-induced concussive impact in animal test subjects. The device and method is capable of producing brain injuries ranging from mild to severe. In order to induce mild TBI, the model requires the animal test subject to wear a custom-designed small animal helmet to protect the head from bruising, yet allowing the brain to sustain an injury that meets the "clinical" criteria of a concussion.

An object of the invention is to produce an animal model with traumatic brain injury to advance research.

Another object of the invention is to inflict measured pressure wave or projectile mediated concussion in laboratory animals.

The present invention provides an experimental tool and method to elucidate the mechanism and pathology of mTBI and facilitate therapeutics research aimed specifically at mTBI treatments.

SUMMARY OF THE INVENTION

In order to study problems of mTBI in the research laboratory, we disclose a $1^{st}$ and $2^{nd}$ generation device, both of which are driven by compressed gases and a method for launching a small projectile designed to impact a target, which includes a protective custom-designed small animal helmet that uses pressure sensor film to measure the force/distribution of the impact pressure on both the outer and inner surfaces of the helmet. The $1^{st}$ generation device uses a method whereby exposure to heat produces rapid sublimation of dry ice contained in a torque-sealed microcentrifuge that generates a strong pressure-wave to cause non-concussive (without a projectile) or concussive (unprotected, directly impact by a projectile) brain injury. The $2^{nd}$ generation device uses a computerized apparatus driven by compressed gases and a method for launching a small projectile designed to impact a target and a protective custom-designed small animal helmet that uses pressure sensor film to measure the force/distribution of the impact pressure on both the outer and inner surfaces of the helmet. The $2^{nd}$ generation device allows for greater manipulation of the injury parameters while providing better control over the "pressure wave" effect. Different degrees of mTBI can be produced by controlling the amount of pressurized gas and the distance of impact from a laboratory animal's head. This method produces clinically relevant mTBI deficits in expected neuropathological (i.e. astrocyte accumulation, nestin and heat shock protein upregulation and neurodegeneration) and neurofunction outcomes (i.e. motor, cognitive and gait disturbances).

Advantages of the present invention over the prior art include, but are not limited to, being more compact and safe, more logistically compatible with small lab spaces, being less inexpensive to set-up and maintain, and being amenable to high throughput experimentation. A salient feature of this invention is that it is capable of reliably and reproducibly generating a true closed-head concussion leading to mild, moderate or severe TBI in animal test subjects with clinically-relevant symptoms and neuropathology. The present invention can induce a closed head trauma that does not require any surgical procedures that is completely non-invasive (i.e. scalp incision, no burr holes for screw sets, or craniotomy).

BRIEF DESCRIPTION OF THE FIGURES

FIG. 8a is a photograph of a coronal section of the brain immunostained for nestin in sham control rat (received anesthesia only) showing no brain injury after 3 days;

FIG. 8b is a photograph of a coronal section of the brain stained immunostained for nestin in sham control rat (received anesthesia only) showing no brain injury after 14 days;

FIG. 8c is a photograph of a coronal section of the brain showing no nestin immunoreactivity induced by pressure wave after 3 days;

FIG. 8d is a photograph of a coronal section of the brain showing no nestin immunoreactivity induced by pressure wave after 14 days;

FIG. 8e is a photograph of a coronal section of the brain showing nestin immunoreactivity induced by a direct impact of the projectile (unprotected) after 3 days;

FIG. 8f is a photograph of a coronal section of the brain showing nestin immunoreactivity induced by a direct impact of the projectile (unprotected) after 14 days;

FIG. 9a is a photograph of a coronal section of the brain immunostained for heat shock protein 27 (HSP27) in sham control rat (received anesthesia only) showing no brain injury after 3 days;

FIG. 9b is a photograph of a coronal section of the brain immunostained for HSP27 in sham control rat (received anesthesia only) showing no brain injury after 14 days;

FIG. 9c is a photograph of a coronal section of the brain showing no HSP27 immunoreactivity induced by pressure wave after 3 days;

FIG. 9d is a photograph of a coronal section of the brain showing no HSP27 immunoreactivity induced by pressure wave after 14 days;

FIG. 9e is a photograph of a coronal section of the brain showing HSP27 immunoreactivity induced by a direct impact of the projectile (unprotected) after 3 days;

FIG. 9f is a photograph of a coronal section of the brain showing HSP 27 immunoreactivity induced by a direct impact of the projectile (unprotected) after 14 days;

FIG. 11a is a photograph of a coronal section of the brain with silver staining in sham control rat (received anesthesia only) showing no neurodegeneration after 14 days;

FIG. 11b is a photograph of a coronal section of the brain with silver staining showing no neurodegeneration induced by pressure wave after 14 days;

FIG. 11c is a photograph of a coronal section of the brain with silver staining showing neurodegeneration induced by a direct impact of the projectile (unprotected) after 14 days;

FIG. 12a is a photograph of relative amounts of cortical GFAP expression in a sham control rat after 3 days;

FIG. 12b is a photograph of relative amounts of cortical GFAP expression in a sham control rat after 14 days;

FIG. 12c is a photograph of relative amounts of cortical GFAP expression induced by pressure wave after 3 days;

FIG. 12d is a photograph of relative amounts of cortical GFAP expression induced by pressure wave after 14 days;

FIG. 12e is a photograph of relative amounts of cortical GFAP expression induced by a direct impact of the projectile (unprotected) after 3 days;

FIG. 12f is a photograph of relative amounts of cortical GFAP expression induced by a direct impact of the projectile (unprotected) after 14 days;

FIG. 13a is a photograph of relative amounts of hippocampal GFAP expression in a sham control rat after 3 days;

FIG. 13b is a photograph of relative amounts of hippocampal GFAP expression in a sham control rat after 14 days;

FIG. 13c is a photograph of relative amounts of hippocampal GFAP expression induced by pressure wave after 3 days;

FIG. 13d is a photograph of relative amounts of hippocampal GFAP expression induced by pressure wave after 14 days;

FIG. 13e is a photograph of relative amounts of hippocampal GFAP expression induced by a direct impact of the projectile (unprotected) after 3 days;

FIG. 13f is a photograph of relative amounts of hippocampal GFAP expression induced by a direct impact of the projectile (unprotected) after 14 days;

DETAILED DESCRIPTION

Definitions

To aid in understanding the invention, several terms are defined below.

"Animal test subject" refers to, without limitation all deuterostomia, including chordates and specifically mammalia, as well as any live organism with a discernable brain capable of being analyzed using known techniques. Said animal test subjects are administered according to U.S. Government principles for the utilization and care of vertebrate animals used in testing, research, and training and in accordance with Public Law 89-544, 1966, as amended, (P.L. 91-579, P.L. 94-279 and P.L. 99-198) 7 U.S.C. 2131 et. seq., and the Guide for the Care and Use of Laboratory Animals, National Academy Press, 1996, Washington, D.C., or succeeding revised editions, as well as applicable laws, regulations and policies.

"Propellant" refers to a gas to include carbon dioxide gas, nitrogen gas, ambient air, gaseous products of a chemical reaction, or the like.

"Propulsive force" refers to the kinetic energy used to eject a projectile from a source.

"Pressure sensor" includes, without limitation, all electromagnetic, resistive, capacitive, and optical sensors; all pressure transducers, pressure transmitters, pressure sensors, pressure indicators, piezoelectric sensor, manometers including sensors that rely on deflection of a membrane under an applied pressure difference; piezoresistors and strain gauges.

"Heat source" includes all means for heat transfer, including but not limited to conduction, convention and radiation means and heat produced from a chemical reaction, as well as any combination of these.

"Sensor film" includes, without limitation, all colorimetric and electronic thin membrane film sensor which are able to indicate or measure pressure magnitude and distribution between contacting surfaces.

Dry Ice Sublimation to Trigger Targeted Release of Small Projectile

Figure 1:
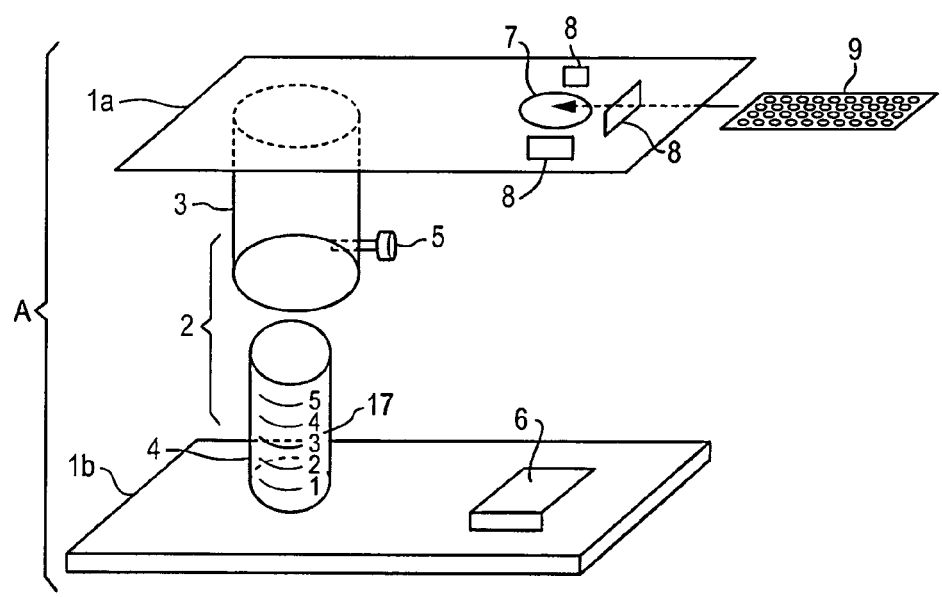
FIG. 1 is a drawing showing a perspective view of a first embodiment of the animal platform of this invention.

FIG. 1 is a view of the platform A made of an upper platform 1a and a lower platform 1b. Mounted on said upper and lower platforms is a raising and lowering device 2. The raising and lowering device 2, as shown, is a sleeve 3 and a cylinder 4. The sleeve and cylinder represents one type of articulating arm. Other articulating arms may also be used for the raising and lowering device. The sleeve 3 receives the cylinder 4 within its inner diameter. A tightening screw 5 is mounted to the sleeve 3 for tightening the sleeve to the cylinder. In this way, the sleeve may be raised and lowered along the length of the cylinder to adjust the height of the upper platform 1a relative to the lower platform 1b. Measuring indicia 17 may be inscribed or applied to the cylinder 4 for measuring distance between the upper and lower platforms.

On the upper platform 1a, an opening 7 is defined therein. Adjacent to at least one side of the opening are one or more slide bar(s) 8 for positioning the head or skull of an animal such as a rodent or other laboratory animal over the opening 7. A screen 9 made of highly perforated metal, plastic or other sturdy material can be positioned over the opening 7 if desired for blocking the projectile yet allowing the pressure wave to pass through.

On the lower platform 1b, a hook 6 is affixed to or integral with the lower platform. The hook 6 is for connecting to a projectile launching device B (FIG. 2) to hold a projectile launching device securely in place under the opening 7 of the upper platform 1a.

Figure 2:
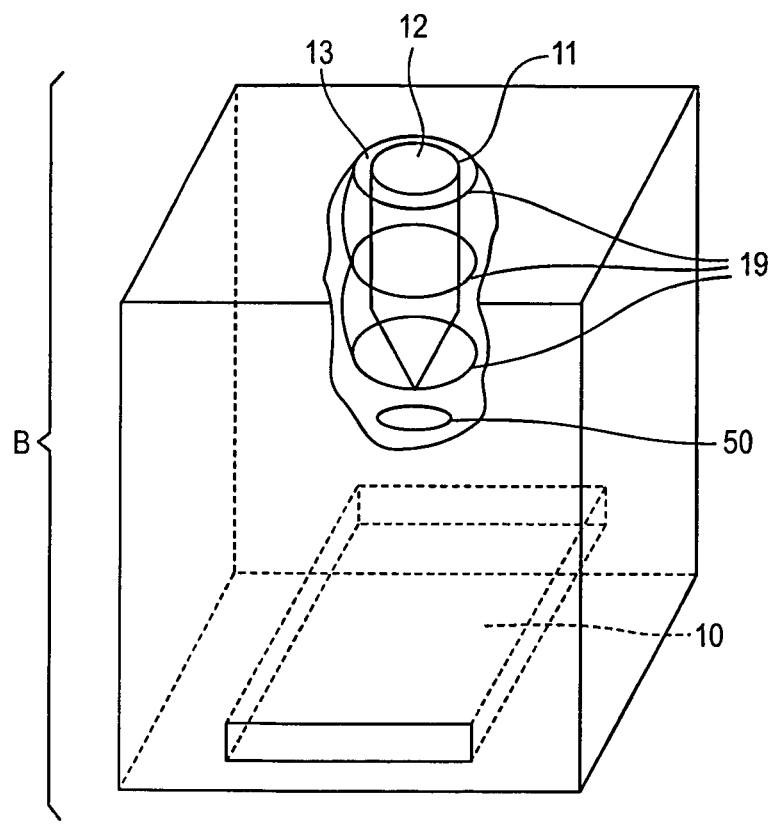
FIG. 2 is a drawing showing a perspective view of one embodiment of the projectile launching device of this invention.
Figure 3:
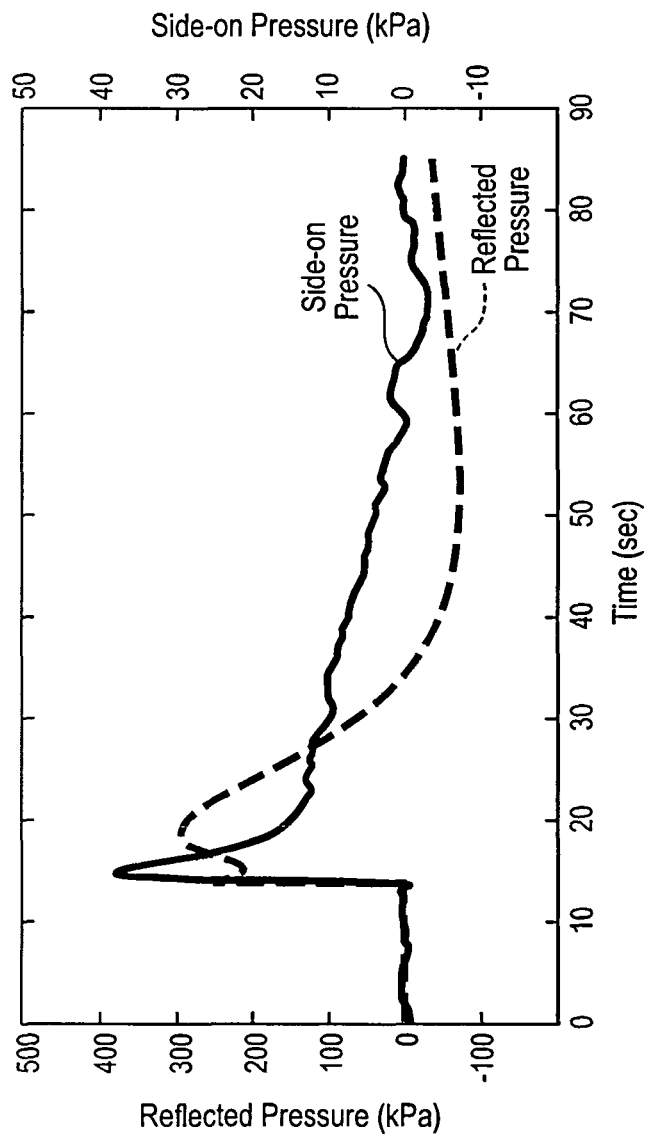
FIG. 3 is a graph of a pressure wave profile generated by the application of the first embodiment of the invention

FIG. 2 is a representation of a projectile launching device B. The projectile launching device B contains a notch 10 that is complimentary to the hook 6 of the lower platform 1b shown in FIG. 1. The notch 10 is for receiving the hook 6 for securely holding the projectile launching device B on the lower platform 1b. Any other mounting device or mechanism may be used that securely holds the projectile launching device to the lower platform in such a manner that it does not move during use.

As shown in FIG. 2, the projectile launching device B is made of a vial or tube 11 having a chamber 12. The chamber is for receiving dry ice (not shown). A heating coil 19 wraps around the tube 11 to heat the tube. A force transducer 50 is also provided for measuring the recoil force of the tube 11.

Figure 4:
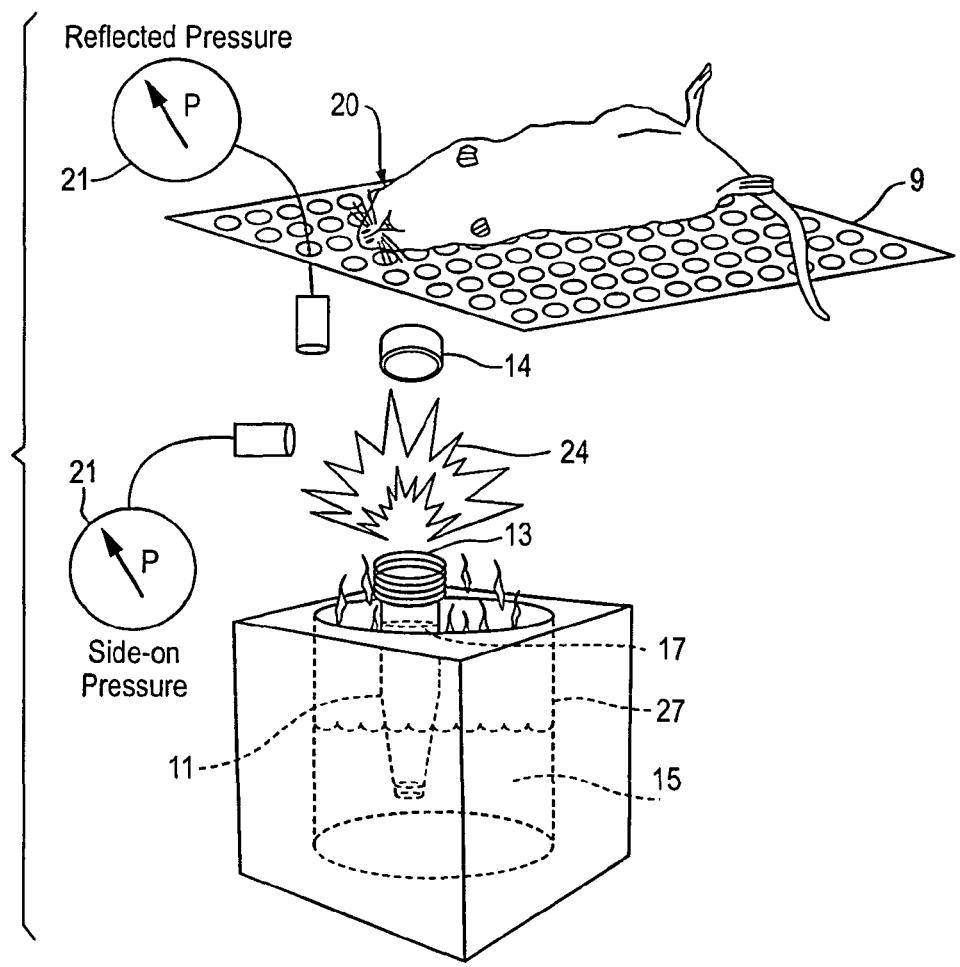
FIG. 4 is a drawing demonstrating the concept of the projectile launching device according to a first embodiment of the invention wherein a pressure wave impacts the animal's head.
Figure 5:
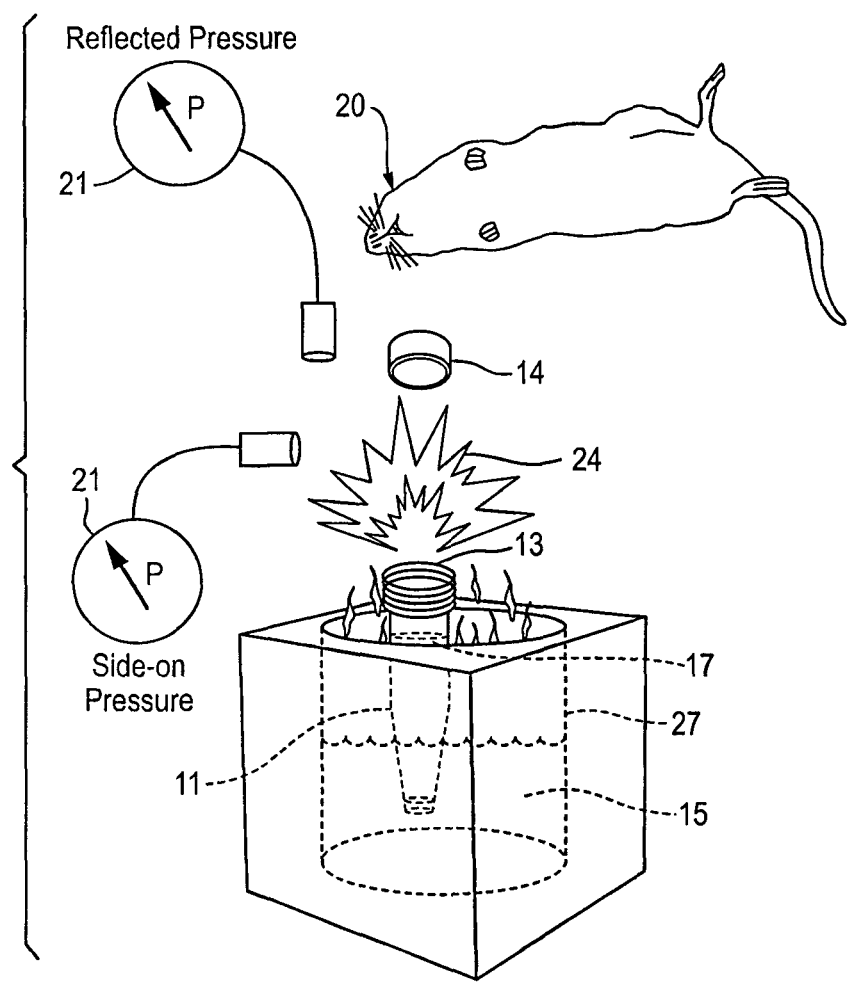
FIG. 5 is a drawing demonstrating the concept of the concussive impact device according to the first embodiment of the invention wherein a projectile impacts the animal's head.

In FIG. 4, according to a first embodiment of the invention; a pressure wave 24 is induced by compressed $CO_2$ generated via sublimation of heated dry ice 17 in the projectile launching device. Dry ice is packed in a tightly sealed microcentrifuge tube 11 and heated in boiling water bath 15 in a tub 27 (FIG. 4 and FIG. 5). The sublimation of dry ice causes the cap 14 (also known as a projectile) on the tube 11 to burst and release a pressure wave 24 through the tube opening 13. A metal screen 9 is used to prevent the cap 14 from hitting the animals' head 20 to insure that the concussive force is in pressure wave form only. Reflected and side-on pressures were measured by pressure sensors located perpendicular and parallel to the direction of the pressure wave respectively 21. The pressures derived from different amounts of dry ice (0.2-

Figure 6:
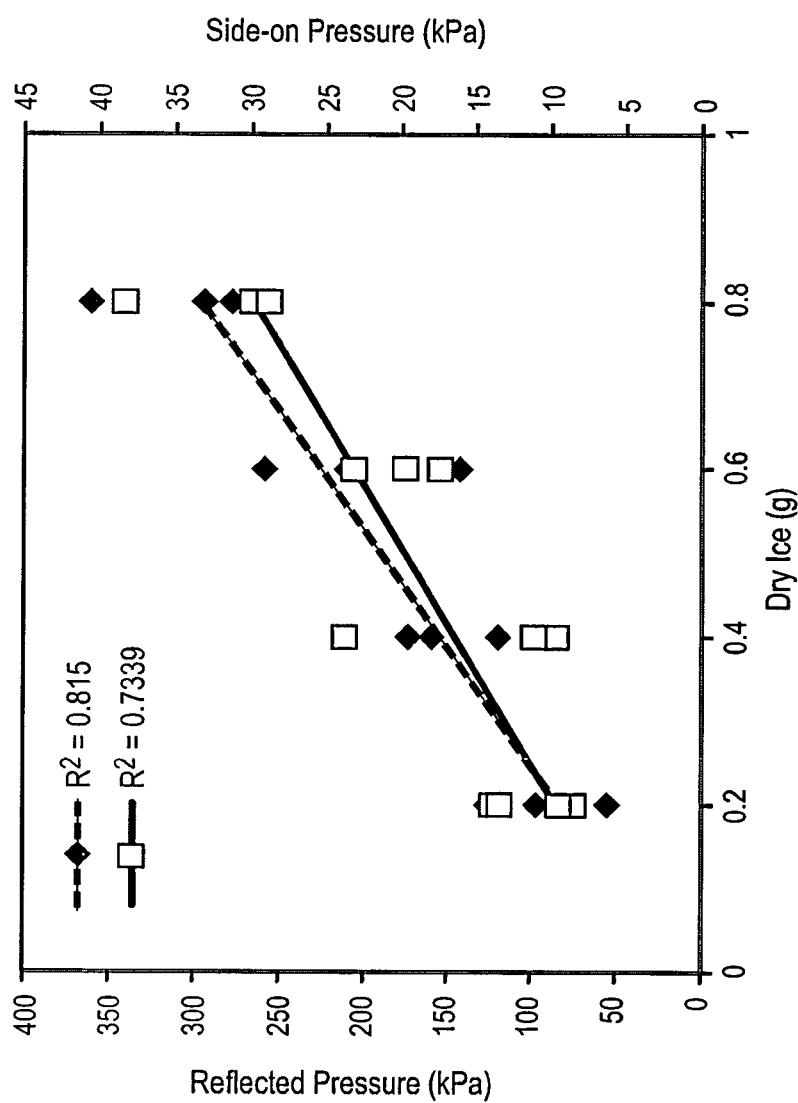
FIG. 6 is a graph showing the correlations between the amount of dry ice and the magnitudes of side-on and reflected pressures.
Figures 7A, 7C, 7E:
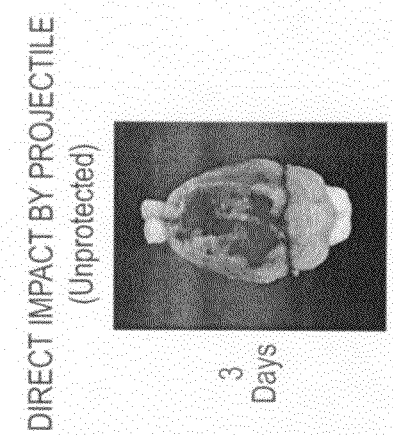
FIG. 7a is a photograph of brain showing no brain injury in sham control rat (received anesthesia only) after 3 days.
FIG. 7c is a photograph of brain showing no gross pathology induced by pressure wave after 3 days.
FIG. 7e is a photograph of brain showing the extent of subdural hemorrhage and contusion caused by a direct impact of the projectile (unprotected) after 3 days.
Figures 7B, 7D, 7F:
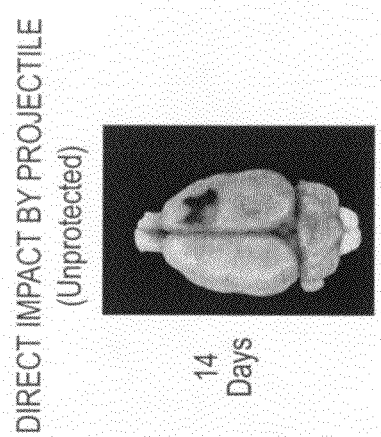
FIG. 7b is a photograph of brain showing no brain injury in sham control rat (received anesthesia only) after 14 days.
FIG. 7d is a photograph of brain showing no gross pathology induced by pressure wave after 14 days.
FIG. 7f is a photograph of brain showing the extent of subdural hemorrhage and contusion caused by a direct impact of the projectile (unprotected) after 14 days.
Figure 10A:
FIG. 10a is a photograph of a coronal section of the brain immunostained for albumin in sham control rat (received anesthesia only) showing no blood brain barrier (BBB) leakage after 3 days.
Figure 10C:
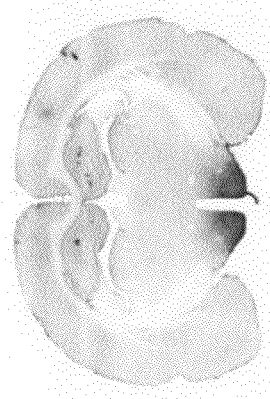
FIG. 10c is a photograph of a coronal section of the brain showing BBB leakage by albumin extravasation induced by pressure wave after 3 days.
Figure 10E:
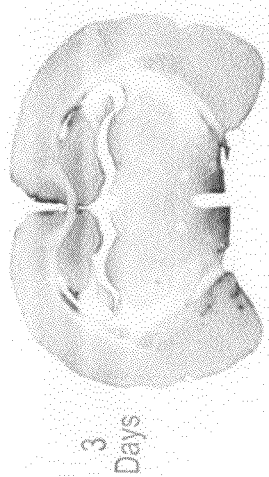
FIG. 10e is a photograph of a coronal section of the brain showing BBB leakage by albumin extravasation induced by a direct impact of the projectile (unprotected) after 3 days.
Figure 10B:
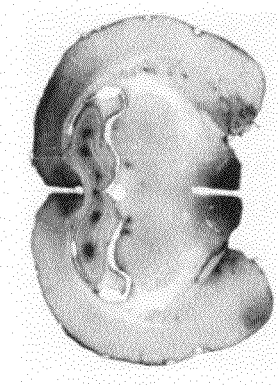
FIG. 10b is a photograph of a coronal section of the brain immunostained for albumin in sham control rat (received anesthesia only) showing no blood brain barrier (BBB) leakage after 14 days.
Figure 10D:
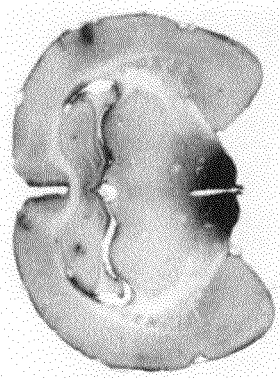
FIG. 10d is a photograph of a coronal section of the brain showing BBB leakage by albumin extravasation induced by pressure wave after 14 days.
Figure 10F:
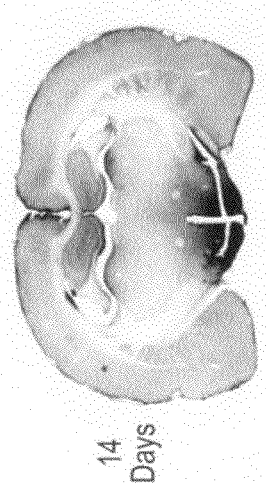
FIG. 10f is a photograph of a coronal section of the brain showing BBB leakage by albumin extravasation induced by a direct impact of the projectile (unprotected) after 14 days.

0.8 g) were measured with the device using a PCB pressure sensor. It was found that the pressure magnitude is proportional to the amount of dry ice used. (FIG. 6).

In an alternate embodiment of the invention, animals are subjected to a pressure wave 24 with the screen 9 removed such that the cap 14 (or projectile) impacts directly on the anesthetized animal's head 20 (FIG. 5).

Figure 14:
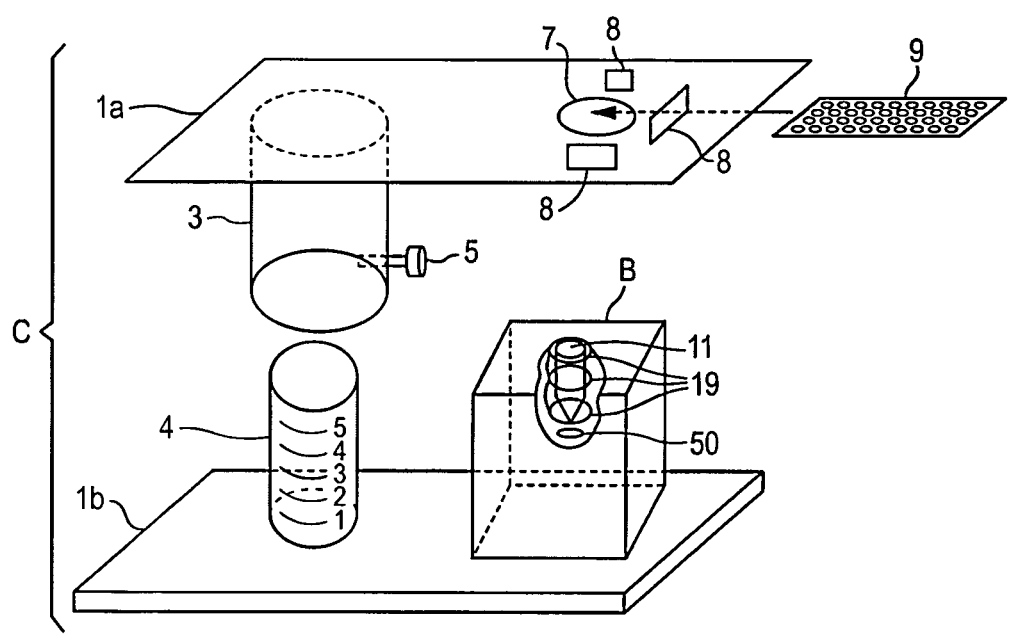
FIG. 14 is a perspective view of the first embodiment of the invention wherein the animal platform and projectile launching device work in conjunction.

As shown in FIG. 14, the injury apparatus C is shown that has a platform A and the projectile launching device B. As shown in FIG. 14, the projectile launching device B is mounted securely to the platform A. The opening 7 in the upper platform 1a is directly above the tube opening 13 so that the projectile 14 will target the animal's head 20 through the opening 7 of the upper platform 1a. The metal screen 9 is removable and can attach to the platform by any manner of attachment. In operation, a laboratory animal's head is placed over the opening 7 and held in place by slide bars 8. Dry ice is placed in the tube 11 and a cap 14 is sealingly secured on the tube. The tightness of the cap is measured by a torque meter. The dry ice in the tube 11 is heated by either a water bath 15 or heating coils 19 or other suitable heating method facilitate the rapid sublimation of dry ice to $CO_2$ gas. The generation of $CO_2$ gas causes pressure to build up within the tube. A force transducer 50 is also provided for measuring the recoil force of the tube 11. The pressure increases enough to cause the cap to burst off the tube in an upward trajectory directed toward the opening 7 in the upper platform 1a and through the opening to hit a laboratory animal's head and cause concussive impact injury. The screen 9 may be placed directly over the opening 7 if only a pressure wave injury is desired by the investigator. The screen 9 prevents the cap 14 from impacting the animal's head but allows the pressure wave generated by the $CO_2$ gas to pass through the screen and directly impact the animal's head.

Figure 16:
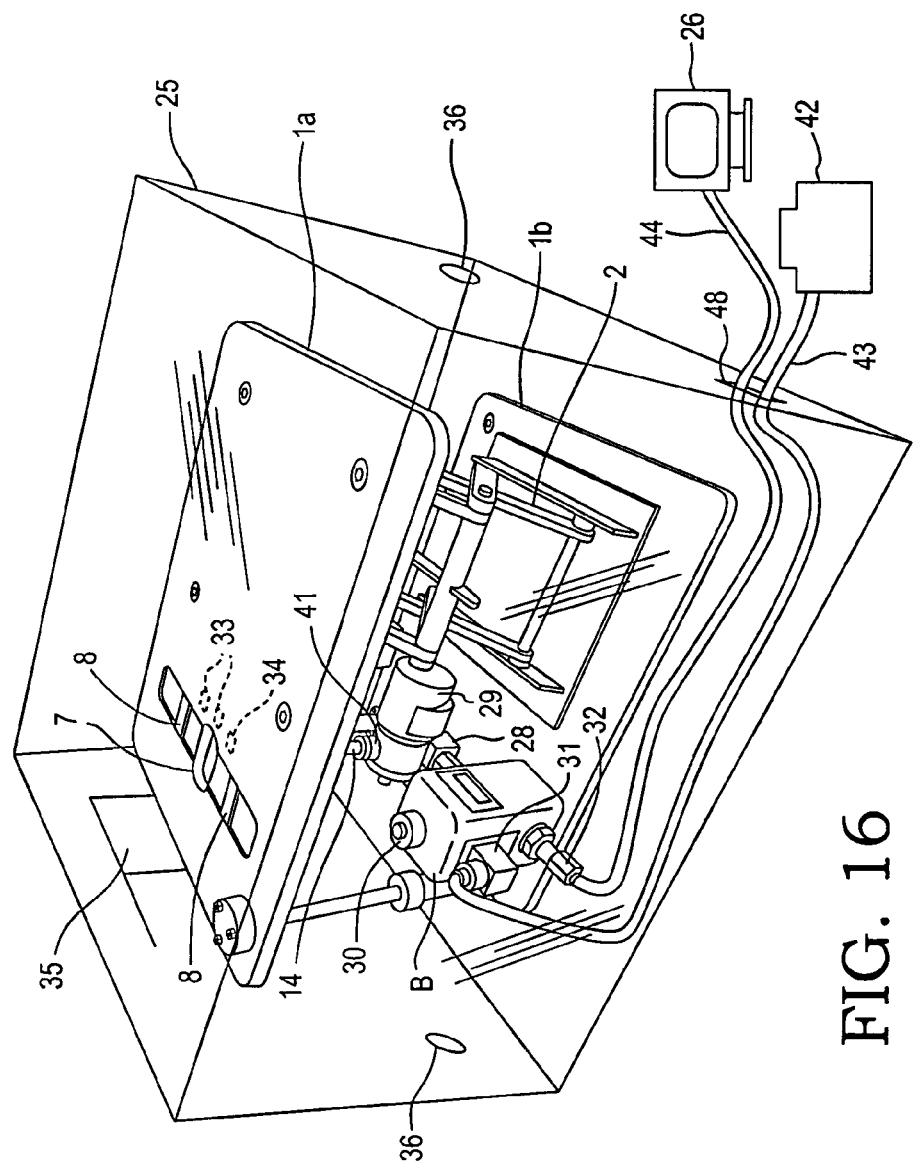
FIG. 16 is a perspective view of the brain injury apparatus of the invention showing a projectile launching device according to the second embodiment of the invention.

In FIG. 16, a plexi-glass viewing chamber 25 covers the brain injury device for added experimenter protection while permitting full visual observation during the procedure.

Figure 15:
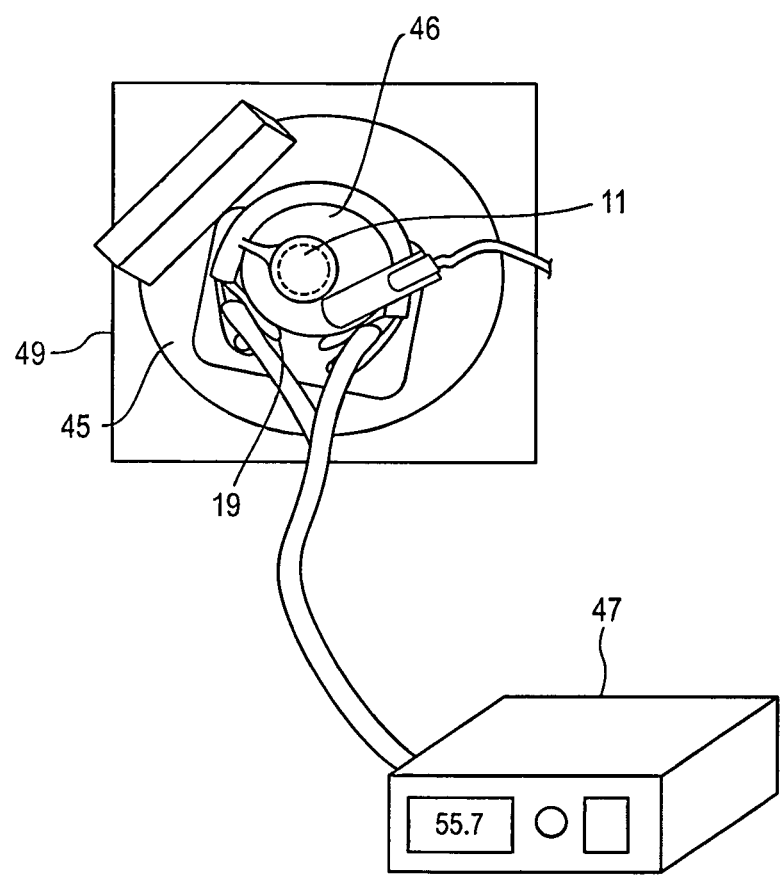
FIG. 15 is top view of the heating unit in the first embodiment of the invention.

The heating unit in FIG. 15 is composed of an outer metal chamber 49 and an inner metal cylinder 46 that holds the microcentrifuge tube 11 containing the dry ice. The inner cylinder is wrapped tightly by an electric heating coil 19. To minimize heat loss to the surroundings, a Bakelite insulator 45 is inserted between the outer chamber 44 and the heating coil 19. The temperature of the heating unit is set at 55.0±5.0° C. and is regulated automatically by a bench top heating controller 47 as shown in FIG. 15 (Omega Engineering Inc., CT).

Various novel aspects of preferred embodiments of the invention are described in the following, non-limiting, examples.

EXAMPLE 1

Method for Inducing Projectile-Mediated Concussive Injury (Unprotected) with the First Embodiment Anesthetized rats (with 2% isoflurane) were exposed to concussive impact via a cap or other projectile 14 targeted and propelled by compressed $CO_2$ gas released from 1.7 g dry ice (FIGS. 1, 2, 4, 5 and 14). A cap 14 was tightly screwed on a microcentrifuge tube 11 using a torque meter and aimed at a target head 20. The targeted head mid-line site was 0.5-1 cm rostral to the interaural line. The tube 11 is heated to induce rapid $CO_2$ sublimation of dry ice 17 and a resultant increase in gas pressure within the tube 11. The pressure builds up in the tube until the thread on the tube fails to hold the cap in place, thus the cap is launched as a projectile in an impact trajectory towards the targeted head 20. Using a high-speed camera (2800 frames/sec). The velocity of the projectile was 47.2±2.3 m/s as estimated based on high speed videos (3 kHz) and it was not related to the amount of dry ice used. The average reflected pressure and side-on pressure were 275 and 30 kPa respectively.

These subjects displayed various degrees of hemorrhage at 3 days and contusion at 14 days (FIGS. 7a-f). Following direct impact of the projectile (unprotected), nestin (FIGS. 8a-f) and HSP 27 (FIGS. 9a-f) upregulation were detected at the impact site at 3 days and expanded to whole cortex at 14 days post injury. In addition, blood brain barrier leakage as revealed by the albumin extravasation was detected at both 3 and 14 days post-injury (FIGS. 10a-f). Delayed neurodegeneration (silver staining) was observed in the thalamus and corpus callosum at 14 days post-injury (FIGS. 11a-c). Cortical astrocytes near the impact site were activated at both 3 days and 14 days, while hippocampal astrocytes were activated at 14 days (FIG. 12a-f). FIGS. 7a-7f, 8a-f, 9a-f, 10a-f, 11a-c, and 12a-f are advantageous for viewing and for making comparisons. These cellular responses and structural damage were not found in sham control animals or animals subjected to pressure wave only.

EXAMPLE 2

Method for Inducing Pressure Wave Concussive Injury the First Embodiment

Anesthetized rats (with 2% isoflurane) were exposed to concussive impact via a cap or other projectile 14 targeted and propelled by compressed $CO_2$ gas released from 1.7 g dry ice (FIGS. 1, 2, 4, 5 and 14). A cap 14 was tightly screwed on a microcentrifuge tube 11 using a torque meter and aimed at a target head 20. The targeted head mid-line site was 0.5-1 cm rostral to the interaural line. The tube 11 is heated to induce rapid $CO_2$ sublimation of dry ice 17 and a resultant increase in gas pressure within the tube 11. The pressure builds up in the tube until the thread on the tube fails to hold the cap in place, thus the cap is launched as a projectile in an impact trajectory towards the targeted head 20. Using a high-speed camera (2800 frames/sec). The velocity of the projectile was 47.2±2.3 m/s as estimated based on high speed videos (3 kHz) and it was not related to the amount of dry ice used. The average reflected pressure and side-on pressure were 275 and 30 kPa respectively. A metal screen 9 was used to block the cap 14 from impacting the animal's head 20 while allowing for the animal's head 20 to expose to the pressure wave generated during the eruption. Slight Increase in astrocyte activation was observed in hippocampus in animals subjected to pressure wave only at 14 days post-injury (FIGS. 13a-f).

EXAMPLE 3

Alternate Device and Method for Inducing Concussive Injury of the First Embodiment A modified projectile launching device B is disclosed (FIG. 14). Instead of using heated liquid, the modified device uses a controlled electrical heating coil 19 to heat and subsequently sublimates the dry ice. A heating plate near the tube 11 may be substituted for a heating coil.

It can be appreciated by one ordinarily skilled in the art that the nature of the tube (size, shape and material) may be changed and still be within the scope of the embodiments of the invention as disclosed herein. Further, the means for producing pressure in this embodiment of the invention may be suitably modified while still remaining within the scope of the preferred embodiment of the invention. In can also be appreciated that means for capturing and/or deflecting the cap or projectile may be modified to suit the needs of the experiment requiring only that the pressure wave be allowed to continue substantially unabated towards the target head. Further still, the method of gathering data by way of this non-limiting example may be modified to suit the specific requirements of the experiment using methods well known in the art.

Compressed $CO_2$ Trigger Mechanism

In a second embodiment of the invention, compressed gas, such as and preferably $CO_2$ gas, was substituted for dry ice sublimation to serve as a trigger mechanism for the projectile. The velocity of the projectile was estimated based on high speed videos. Impact force and pressures were measured at different $CO_2$ input pressures.

According to the second embodiment of the invention, a brain injury device C has a projectile launching device B. The projectile launching device B is computerized to launch a small projectile 14 using compressed gases. The projectile launching device can be used to deliver a concussive impact traumatic brain injury.

As shown in FIG. 16, a brain injury apparatus C has an upper platform 1a, preferably made of steel or other durable and strong material and a lower platform 1b. The upper platform 1a can be adjusted to different heights, preferably adjustable between 2-5 inches with the raising and lowering device 2. An opening 7 is defined by the platform 1a. The opening is preferably ovular in shape. The opening 7 allows for exposure of an animal's head from the bottom of the upper platform 1a. The opening is preferably at one end of the platform.

The raising and lowering device 2 can be manual or electronic. It can also be controlled by a computer. The type of raising and lowering device is not particularly important as long as it can operate to raise and lower the platform in relation to the projectile launching device and be locked into position.

A temperature sensor 33 and a pressure transducer 34 (to measure reflected pressure) are mounted near or on the underside of the upper platform (preferably parallel to the underside of the upper platform 1a) near the ovular opening 7. A second pressure transducer 34 (to measure side-on pressure) is also mounted near the underside of the platform 1a (preferably on a metal plate attached to the underside of the platform) near the opening 7 that is perpendicular to the platform 1a. The temperature and pressure data are collected by a data acquisition system and displayed on a computer 26. This data can be transported from the computer controlled interface 31 to a computer via a data transfer means 44. A data transfer means is any means known in the art that transports data such as but not limited to cable, Bluetooth, wirelessly. The computer can be part of the brain injury apparatus or can be a remote computer such as personal computer (PC).

FIG. 16 also shows the gas source (compressed gas cylinders or cartridges) 42 connected to the compressed gas inlet 32 via a hose 43. Slide bars 8 help to hold an animal's head over the opening 7.

Figure 17:
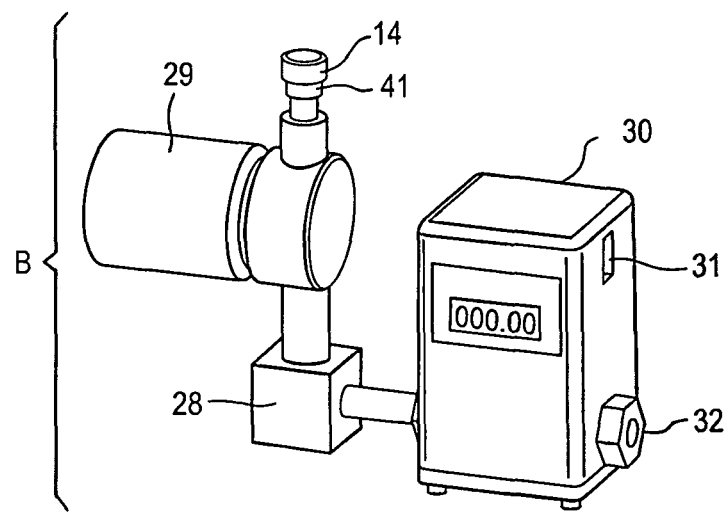
FIG. 17 is a perspective view of the projectile launching device of a second embodiment of the invention.

Referring to FIGS. 16 and 17, a projectile launching device B is positioned and mounted directly underneath the opening 7 defined by the platform 1a. The projectile launching device B has a interchangeable projectile mount 41 to hold the projectile 14 in place, an electrically actuated solenoid pressure release valve 29, a gas reservoir 28, electro-pneumatic pressure control valve 30, computer control interface 31 (serial port), instrument controlling computer 26, and an inlet for compressed gases 32 as shown in FIG. 17.

The input pressure is directly proportional to the projectile velocity and impact force. The input pressure is user-selectable between 25 to 150 psi, which corresponds to forces ranging from 50 to 150 N and projectile velocities ranging from 20 to 60 m/s. An experiment is initiated by entering the desired input pressure in the software module. When the desired input pressure has been reached, the computer controlled mechanism releases the projectile from the projectile launching device.

The platform and the projectile launching device can be contained within an enclosed anesthesia transparent viewing chamber 25 such as that shown in FIG. 15. The chamber can be plexiglass or other transparent material to permit viewing of the procedure. The dimensions of the chamber are preferably 15 inches wide by 15 inches long by 18 inches high. The chamber 25 preferably has one or more doors 35 and more preferably two sliding doors 35 to allow the manipulation of the animal and projectile placement. The chamber also preferably has ventilation means in the form of one or more inlet or outlet holes 36 to permit the inlet or outlet of a volatile anesthetic agent. The holes 36 are defined by the chamber and are preferably at opposite ends of the chamber.

EXAMPLE 4

Device Characterization of Second Embodiment

The velocity of the projectile was estimated based on high speed videos. Impact force and pressures were measured at different $CO_2$ input pressures. The device produced a range of projectile velocity and impact force dependent on the $CO_2$ input pressure, as shown in FIG. 4. Specifically, an input pressure of 56 psi produced a velocity 39.93±1.38 m/s and impact force 171.84±15.49N whereas an input pressure of 25 psi produced a velocity 22.34±0.08 m/s and impact force 55.04±7.85N. In contrast, the average magnitude and duration of both reflected (2.95±0.19 kPa, 7.12±0.55 s) and side-on pressures (2.50±0.30 kPa, 12.89±1.52 s) did not vary with $CO_2$ input pressure.

In summary, the linear relationship between input pressure of compressed gas and impact force/projectile velocity in the second embodiment facilitates greater manipulation of the injury parameters. In addition, the pressure wave generated from the release of compressed $CO_2$ is of low magnitude and is not related to the input pressure. Thus, the injury is purely impact-induced and any "pressure wave" effect is minimal.

Helmet Testing

Figure 18:
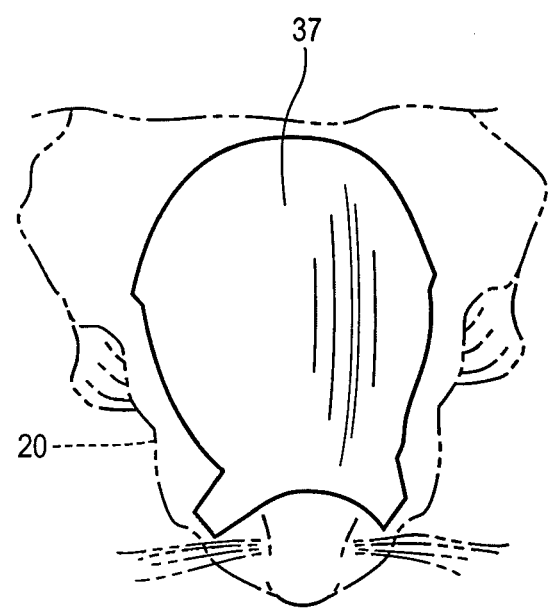
FIG. 18 is a perspective view of a helmet mounted on a head of an animal as used in the invention.
Figure 19:
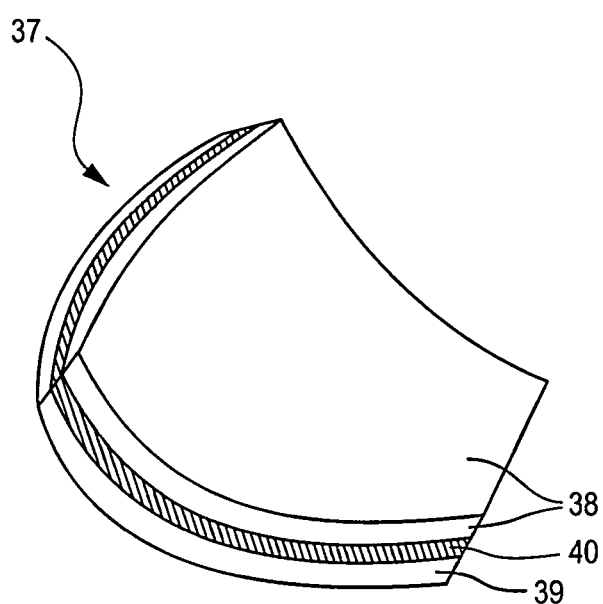
FIG. 19 is a side view of the helmet of the invention showing the layering of the helmet substrate and the pressure sensor films.

As shown in FIGS. 18-19, a protective small animal or laboratory helmet 37 is made of a substrate 40 made of composite materials. The helmet is used in conjunction with the present brain injury apparatus. The helmet may have one or more pressure sensor films applied thereto for measuring pressure magnitude/distribution. The helmet is attached to the subject's head by straps, string, tape or conforming fit.

An inner pressure sensor film 38 and an outer pressure sensor film 39 may be applied to or made integral with the helmet substrate materials 40 during manufacturing. The pressure sensor films measure the pressure magnitude/distribution during impact on both the outer and inner surfaces of the helmet.

The animal helmets are constructed based on the dimension of the life size mold of an adult test animal type and breed. In the present invention, for example, the helmet was designed to fit a 300 g Sprague-Dawley male rat. The helmet can be designed to fit other types of animals. The helmet substrate is fabricated from but not limited to, the following materials: Carbon, glass, Kevlar and Dyneema.

The thicknesses of the helmet and the sensor film are about 0.91 mm and 0.18 mm respectively.

Specific examples of composite materials for the helmet are as follows:

1 layer 0-90 (deg) woven 7781 S-2 glass; 1 layer 0 (deg) uni-IM7 381 Carbon; 1 layer 90 (deg) uni-IM7 381 Carbon; 1 layer 0-90 (deg) woven 7781 S-2 glass 2 layers 0-90 (deg) woven 7781 S-2 glass; 1 layer 0 (deg) uni-IM7 381 carbon; 1 layer 90 (deg) uni-IM7 381 carbon; 2 layer 0-90 (deg) woven 7781 S-2 glass 4 layer 0-90 (deg) woven 707 Kevlar; 2 layer 0-90 (deg) woven 7781 S-2 glass 4 layers 0-90 (deg) woven Carbon-SC 15 Toughened Epoxy Colorimetric pressure sensor films 38 and 39 are laid on the inner and outer side of the helmet to form a three layer helmet. The type of pressure sensor film used in the invention is Fujifilm Prescale Film. Pressure data (magnitude, distribution), contact area and impact force were analyzed using Topaq Pressure Analysis System (Sensor Products, Inc.). Upon impact, the inner film 38 reveals the pressure distribution profile, contact area, pressure and force magnitudes, that occurred between the helmet and rat head and outer film 39 reveals the same data that occurred between the helmet and projectile.

EXAMPLE 5

Proof of Principle Injury Data of Second Embodiment

Helmets substrates constructed of three different composite materials, (A) woven glass/carbon, (B) fiber glass pre-impregnated with resin, (C) Dyneema/woven carbon fiber with toughened epoxy resin, were tested for protective performance. Strength and modulus of these composites were determined by tensile testing using the testing standard ASTM D3039 with Instron material testing system (10 kN load cell). To evaluate the helmet performance, rats were assigned into four groups (n=3/group): Sham control (received anesthesia only), Helmet A, Helmet B and Helmet C. The helmet groups were subjected to PCI (right, 45°) once daily for consecutive five days. At 24 h after the 5th hit, brains were harvested after transcardial perfusion, post-fixed in 4% paraformaldehyde and cryoprotected in 20% sucrose solution. Coronal sections (40 μm) of cerebrum were immunostained for glial fibrillary acidic protein (GFAP) and β-amyloid precursor protein (βAPP). Immunoreactivities of GFAP and βAPP were quantified using threshold analysis and were expressed as % Area (100%*thresholded pixel/area).

The elastic modulus and maximum stress of Helmet A were much lower than those of Helmet B and C, indicating that material used for Helmet A are flexible and can be deformed by a small amount of stress whereas, Helmet B and C are relatively stiff.

|  | Max. Stress (MPa) | Max. Strain (%) | Elastic Modulus (MPa) |
|---|---|---|---|
| Helmet A | 14.3 ± 0.5 | 3.9 ± 0.2 | 362.9 ± 2.3 |
| Helmet B | 303.2 ± 5.5 | 4.7 ± 0.2 | 6525.7 ± 174.9 |
| Helmet C | 133.9 ± 2.4 | 4.6 ± 0.1 | 2928.0 ± 33.6 |

The average pressure applied to the helmet's outer surface by the projectile was 4747±60 kPa. All helmets effectively protected against skull fracture, subarachnoid hemorrhage and contusion. Pressure data of the inner surface demonstrated that helmet A (449±6 kPa) yielded the most consistent pressure distribution and the highest force magnitude (160±21N). Helmet A's material is flexible and can be deformed by a small amount of stress (low elastic modulus). Thus, it transfers load efficiently from the projectile impact to the animal's head that is critical for producing concussion in the absence of any overt pathology. In contrast, the other 2 helmets did not yield a satisfactory pressure distribution on the inner surface indicating these helmets were relatively stiff and may not effectively transfer the load to the rat head.

|  | Average Pressure (kPa) | Contact Area (cm$^2$) | Force (N) |
|---|---|---|---|
| Between Projectile and Helmet |  |  |  |
| Helmet A | 4894.73 ± 87.22 | 1.15 ± 0.08 | 567.19 ± 45.55 |
| Helmet B | 5209.20 ± 149.48 | 1.14 ± 0.09 | 592.90 ± 47.11 |
| Helmet C | 4481.04 ± 106.39 | 1.18 ± 0.09 | 527.74 ± 47.11 |
| Between Helmet and Animal's Head |  |  |  |
| Helmet A | 449.19 ± 5.72 | 3.99 ± 0.81 | 160.45 ± 21.26 |
| Helmet B | 430.72 ± 9.31 | 3.28 ± 0.77 | 136.03 ± 29.54 |
| Helmet C | 415.68 ± 8.96 | 3.21 ± 1.92 | 53.65 ± 10.41 |

Figure 20:
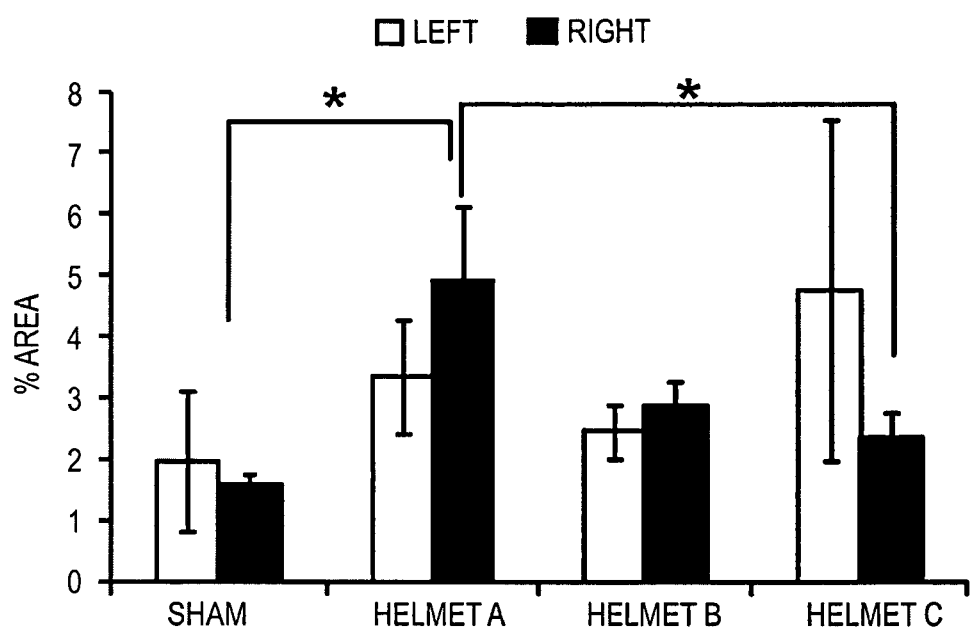
FIG. 20 is a graph showing the hippocampal GFAP Immunoreactivity in rats subjected to concussive impact injury with different helmets.
Figure 21A:
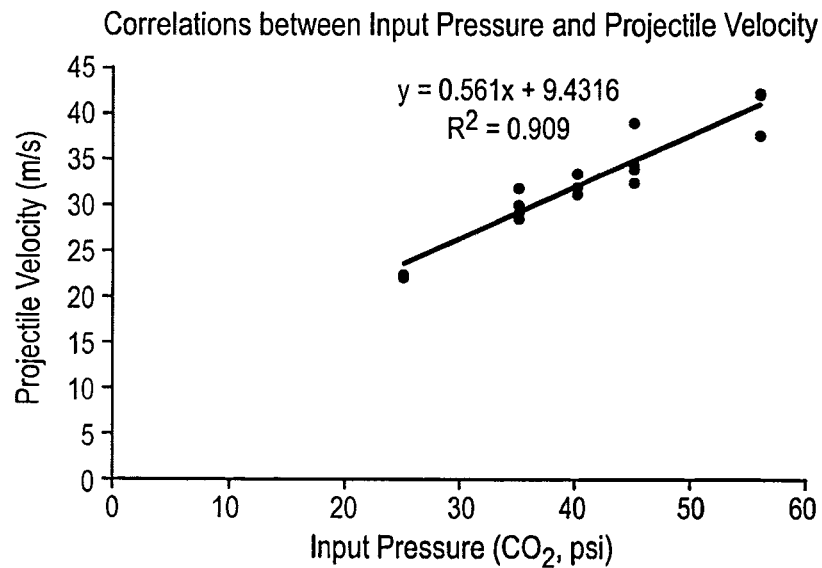
FIG. 21a is a graph showing the correlation between input pressure and projectile velocity of the projectile launching device according to a second embodiment of the invention.
Figure 21B:
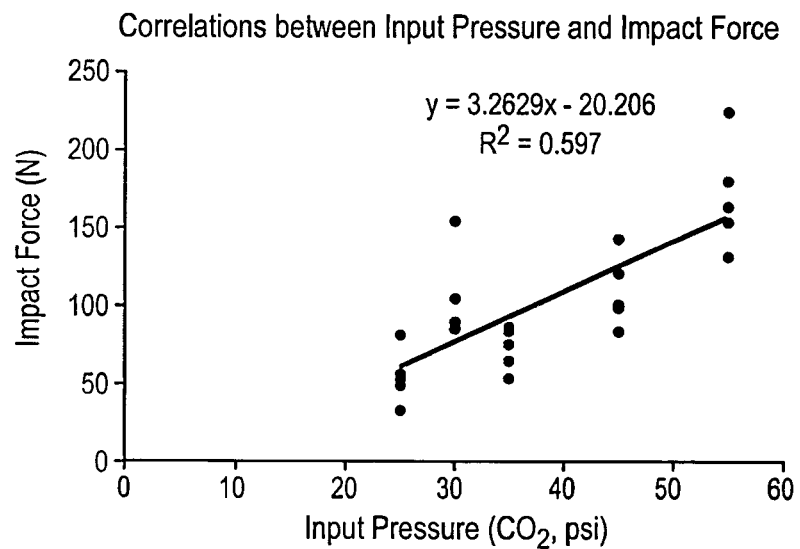
FIG. 21b is a graph showing the correlation between input pressure and impact force of the projectile launching device according to a second embodiment of the invention.
Figure 21C:
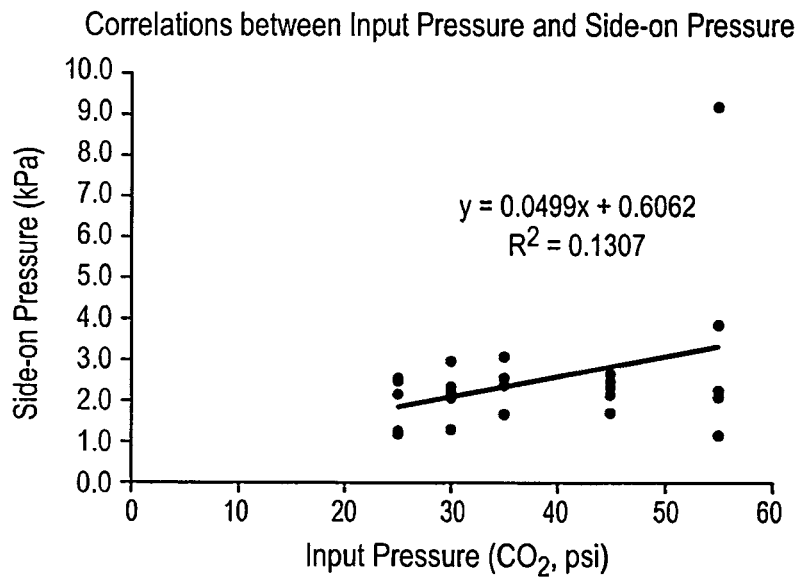
FIG. 21c is a graph showing the correlation between input pressure and side-on pressure of the projectile launching device according to a second embodiment of the invention.
Figure 21D:
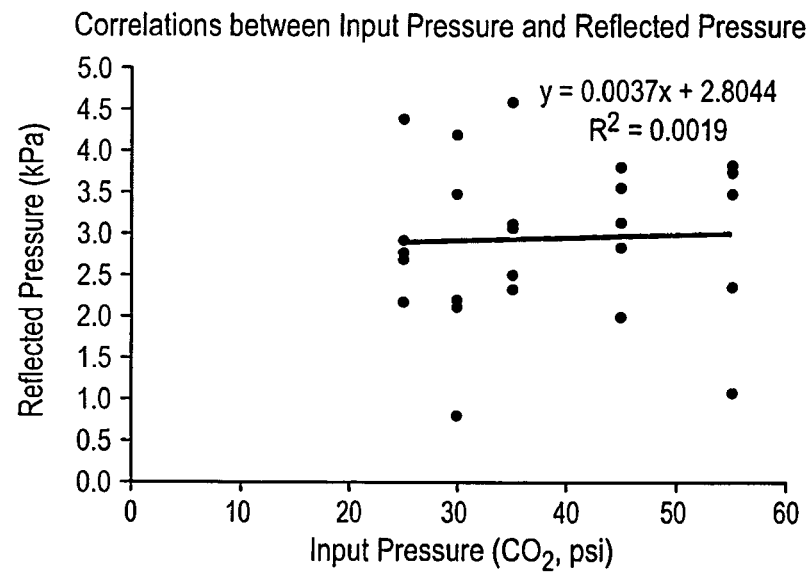
FIG. 21d is a graph showing the correlation between input pressure and reflected pressure of the projectile launching device according to a second embodiment of the invention.

Significant increase in GFAP was detected in the right hippocampus of Helmet A group, compared with sham ($p<0.01$) and Helmet C group ($p<0.05$). No significant increases in βAPP immunoreactivity were detected at 24 h. See FIG. 20.

The preferred helmet is made of fiberglass and carbon weave because it exhibited low elastic modulus and strength while demonstrating consistent load transfer efficiency that is critical for producing concussion without overt pathology. Histopathology results showed that astrocyte activation increased significantly in hippocampus of the rats with Helmet A at 24 hours following repeated projectile concussive impact injury.

Overall the combination use of the helmet and the compressed $CO_2$ projectile launching device show a good concussive model with controlled, reproducible and quantifiable results. The intensity of the force can be titrated, potentially producing a wide spectrum of concussive injury severities for further study.

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

REFERENCES

The teachings of the references cited herein are incorporated herein in their entirety:

What is claimed is:

1. An apparatus for inflicting brain injury on a laboratory animal comprising:
   a platform for supporting said laboratory animal, said platform defining an opening for positioning a head of said laboratory animal over the opening;
   a projectile;
   a projectile launching device orientated below said opening of said platform, said projectile launching device having a trigger mechanism for propelling said projectile directly at and/or through said opening of said platform, said projectile launching device comprising:
      a vial of dry ice having an opening at one end;
      a heater source for heating said vial to generate gas from said dry ice,
      wherein said $CO_2$ gas generated from said dry ice is capable of launching said projectile from said opening of said vial.

2. The apparatus of claim 1, wherein said heater source comprises a hot water bath.

3. The apparatus of claim 1, wherein said heater source comprises a heating coil wrapped around said vial of dry ice.

4. The apparatus of claim 1, wherein said heater source comprises a heating element.

5. The apparatus of claim 1, wherein said projectile is a cap attached to said opening of said vial via frictional force or torque applied on screw threads of said vial.

6. The apparatus of claim 1, wherein when said projectile launching device launches said projectile, a pressure wave is generated in the direction of said opening by said platform.

7. The apparatus of claim 1, wherein said platform further comprises a screen attached to said platform directly over said opening for deflecting said projectile.

8. The apparatus of claim 7, wherein said screen is mounted to said platform in a manner so that it can slide back and forth over said opening.

9. The apparatus of claim 7, wherein said screen is a metal screen.

10. The apparatus of claim 1, further comprising a force transducer for measuring the recoil force of the tube during the projectile's launch; and a pressure sensor for measuring one or more of a pressure generated by said moving projectile.

11. The apparatus of claim 1, wherein said platform comprises an upper and lower platform, said upper platform defining said opening therein, said lower platform being able to securely attach said projectile launching device to said lower platform in a position directly below said opening and an ability to raise and lower said upper platform relative to said lower platform.

12. The apparatus of claim 11, wherein said platform has an articulating arm for raising and lowering the upper platform relative to the lower platform.

13. The apparatus of claim 12, wherein said articulating arm is manually operated or electronically operated.

14. The apparatus of claim 1, wherein said platform has slide bars in the vicinity of said opening for positioning said animal's head directly over said opening.

15. The apparatus of claim 1, wherein said apparatus further comprises a transparent viewing chamber for enclosing said platform and said projectile launching device.

16. The apparatus of claim 15, wherein said viewing chamber further comprises inlet or outlet holes for providing ventilation and one or more access doors.

17. The apparatus of claim 1, further comprising a computer in communication with said apparatus for recording CO2 pressure and/or pressure wave data.

18. A kit comprising the apparatus of claim 1 and a helmet for attaching to said laboratory animal's head.

19. The kit of claim 18, wherein said helmet has pressure sensor film attached to an inside surface and an outside surface of said helmet for measuring impact of said projectile from said projectile launching device.

20. The apparatus of claim 1, wherein said means for launching said projectile comprises compressed $CO_2$.

21. The apparatus of claim 1, wherein said apparatus further comprises a temperature sensor.

22. The apparatus of claim 1, wherein said apparatus further comprises a pressure transducer.

23. The apparatus of claim 1, wherein said projectile launching device comprises:
   a compressed gas source for delivering compressed gas;
   a gas reservoir;
   a projectile mount for holding said projectile;
   an electro-pneumatic pressure control valve between said compressed gas source and said gas reservoir for transferring said compressed gas from said gas source to said gas reservoir;
   an electrically actuated solenoid pressure release valve between said compressed gas reservoir and said projectile mount for transferring said compressed gas from said gas reservoir to said projectile mount, wherein in use said compressed gas propels said projectile from said projectile mount.

24. The apparatus of claim 23, wherein the projectile mount is interchangeable.

25. The apparatus of claim 23, further having a software module for controlling said input pressure of said gas.

26. The apparatus of claim 23, wherein said input pressure is selectable between 25 to 150 psi, which corresponds to forces ranging from 50 to 150 N.

27. The apparatus of claim 23, further comprising a computer and a computer interface between said computer and said electro-pneumatic pressure control valve for controlling an input pressure of said gas impacting said projectile.

28. The apparatus of claim 27, wherein said computer controls the launching of said projectile.

29. The apparatus of claim 1, wherein said apparatus is capable of launching said projectile at a velocity 20.3 to 60.5 m/s.

30. An apparatus for inflicting brain injury on a laboratory animal comprising:
   a platform for supporting said laboratory animal, said platform defining an opening for positioning a head of said laboratory animal over the opening;
   a projectile;
   a projectile launching device orientated below said opening of said platform, for propelling said projectile directly at and/or through said opening of said platform, wherein said projectile launching device comprises:
      a vial of dry ice having an opening at one end;
      a heater source for heating said vial to generate $CO_2$ gas from said dry ice,
      wherein said $CO_2$ gas generated from said dry ice is capable of launching said projectile from said opening of said vial.

31. A method of inflicting brain injury on a laboratory animal comprising:
   providing the apparatus of claim 30;
   providing a laboratory animal;
   positioning a head of said laboratory animal over the opening defined by said platform;
   heating said dry ice to generate said $CO_2$ gas inside said vial;

launching said projectile from said vial by pressure generated from said $CO_2$ gas toward said opening and impacting said head of said laboratory animal with said projectile.

32. The method of claim 31, further comprising the step of placing a helmet on the head of said laboratory animal prior to positioning said head over said opening, said helmet comprising
   a substrate having a first side and a second side
   sensor films on said first and said second sides.

33. The method of claim 31, further comprising the step of measuring pressure of said pressure wave with at least one pressure sensor.

34. The method of claim 31, further comprising the step of modulating a propelling force of the projectile.

35. The method of claim 31, further comprising the step of measuring the extent of traumatic brain injury in said laboratory animal.

36. A method of inflicting brain injury on a laboratory animal comprising:
   providing the apparatus of claim 30;
   providing a mesh and positioning said mesh over said opening to deflect said projectile;
   providing a laboratory animal;
   positioning a head of said laboratory animal over the opening defined by said platform;
   heating said dry ice to generate said $CO_2$ gas inside said vial;
   launching said projectile from said vial toward said opening with pressure generated from said $CO_2$ gas, wherein a pressure wave is generated by the launched projectile that impacts said head of said laboratory animal and said projectile is deflected by said mesh.

37. The method of claim 36, further comprising the step of placing a helmet on the head of said laboratory animal prior to positioning said head over said opening, said helmet comprising
   a substrate having a first side and a second side
   sensor films on said first and said second sides.

38. The method of claim 36 further comprising the step of measuring pressure of said pressure wave with at least one pressure sensor.

39. The method of claim 36, further comprising the step of modulating a propelling force of the projectile.

40. The method of claim 36, further comprising the step of measuring the amount of traumatic brain injury in said laboratory animal.

41. An apparatus for inflicting brain injury on a laboratory animal comprising:
   a platform for supporting said laboratory animal, said platform defining an opening for positioning a head of said laboratory animal over the opening;
   a projectile;
   a projectile launching device orientated below said opening of said platform, for propelling said projectile directly at and/or through said opening of said platform, wherein said projectile launching device comprises:
      a compressed gas source for delivering compressed gas;
      a gas reservoir;
      a projectile mount for holding said projectile;
      an electro-pneumatic pressure control valve between said compressed gas source and said gas reservoir for transferring said compressed gas from said gas source to said gas reservoir;
      an electrically actuated solenoid pressure release valve between said compressed gas reservoir and said projectile mount for transferring said compressed gas from said gas reservoir to said projectile mount, wherein in use said compressed gas propels said projectile from said projectile mount.

42. The apparatus of claim 41, wherein the projectile mount is interchangeable.

43. The apparatus of claim 41, further having a software module for controlling said input pressure of said gas.

44. The apparatus of claim 41, wherein said input pressure is selectable between 25 to 150 psi, which corresponds to forces ranging from 60 to 470 N.

45. The apparatus of claim 41, further comprising a computer and a computer interface between said computer and said electro-pneumatic pressure control valve for controlling an input pressure of said gas impacting said projectile.

46. The apparatus of claim 41, wherein said computer controls the launching of said projectile.

47. A method of inflicting brain injury on a laboratory animal comprising:
   providing the apparatus of claim 41;
   providing a laboratory animal;
   positioning a head of said laboratory animal over the opening defined by said platform;
   providing said $CO_2$ gas from said gas source through said electro-pneumatic pressure control valve, said gas reservoir and pressure release valve to said projectile mount;
   launching said projectile from said projectile mount through said opening and impacting said head of said laboratory animal with said projectile with pressure from said $CO_2$ gas.

48. The method of claim 47, further comprising:
   providing a computer and a computer interface between said computer and said electro-pneumatic pressure control valve; and
   controlling an input pressure of said gas impacting said projectile with said computer.

49. The method of claim 48, further comprising the step of placing a helmet on the head of said laboratory animal prior to positioning said head over said opening, said helmet comprising
   a substrate having a first side and a second side
   sensor films on said first and said second sides of said substrate.

50. The method of claim 47, further comprising the step of measuring the amount of traumatic brain injury in said laboratory animal.

* * * * *